United States Patent
Sadoul et al.

(10) Patent No.: US 6,869,600 B1
(45) Date of Patent: Mar. 22, 2005

(54) COMBINED TREATMENT OF MULTIPLE SCLEROSIS

(75) Inventors: Rémy Sadoul, Montbonnot-Saint Martin (FR); Sonia Pagliusi, Vessy (CH)

(73) Assignee: Applied Research Systems ARS Holding N.V. (AN)

( * ) Notice: Subject to any disclaimer, the term of this patent is extended or adjusted under 35 U.S.C. 154(b) by 0 days.

(21) Appl. No.: 09/958,351
(22) PCT Filed: Mar. 20, 2000
(86) PCT No.: PCT/EP00/02443

§ 371 (c)(1),
(2), (4) Date: Dec. 20, 2001

(87) PCT Pub. No.: WO00/61176
PCT Pub. Date: Oct. 19, 2000

(30) Foreign Application Priority Data

Apr. 8, 1999 (EP) .............................. 99106929

(51) Int. Cl.[7] ...................... A61K 38/00; C07K 14/565; C07K 14/575; C07K 14/61
(52) U.S. Cl. ...................... 424/85.4; 424/85.6; 514/2; 530/399
(58) Field of Search ................. 424/85.4, 85.6, 424/85.1; 514/2; 530/399, 300, 350, 398

(56) References Cited

U.S. PATENT DOCUMENTS

| | | | |
|---|---|---|---|
| 4,898,856 A | | 2/1990 | Aroonsakul |
| 5,370,870 A | * | 12/1994 | Wong .......................... 424/85.1 |
| 5,426,096 A | * | 6/1995 | Sonksen et al. .............. 514/12 |
| 5,780,021 A | * | 7/1998 | Sobel .......................... 424/85.4 |
| 5,846,526 A | * | 12/1998 | Cummins .................... 424/85.7 |
| 6,187,750 B1 | * | 2/2001 | Chein .......................... 514/12 |
| 6,297,212 B1 | * | 10/2001 | Fahy ............................ 514/2 |
| 6,485,480 B1 | * | 11/2002 | Berwitt ........................ 604/500 |

FOREIGN PATENT DOCUMENTS

WO    WO 92/07578    5/1992

OTHER PUBLICATIONS

Edwards et al. (Jun. 1992) "In Vivo Administration of Recombinant Growth Hormone or Gamma Interferon Activates Macrophages: Enhanced Resistance to Experimental . . . " Infection and Immunity 60(6): 2514–2521.*

Cleland and Jones (Oct. 1996) "Stable Formulations of Recombinant Human Growth Hormone and Interferon–g for Microencapsulation in Biodegradable Microspheres." Pharmaceutical Research 13(10): 1464–1475.*

Ye et al., In vivo actions of insulin–like growth factor–I (IGF–I) on brain myelination: studies of IGF–I and IGF binding protein–1 (IGFBP–1) transgenic mice, *The Journal of Neuroscience*, 15(11):7344–7356 (1995).

Yao et al., Insulin–like growth factor I treatment reduces demyelination and up–regulates gene expression of myelin–related proteins in experimental autoimmune encephalomyelitis, *Proc. Natl. Acad. Sci. USA*. 92:6190–6194 (1995).

(List continued on next page.)

*Primary Examiner*—Elizabeth Kemmerer
*Assistant Examiner*—Christopher James Nichols
(74) *Attorney, Agent, or Firm*—Browdy and Neimark, P.L.L.C.

(57) ABSTRACT

The use of growth hormone (GH) together with an interferon (IFN) to produce a pharmaceutical composition for treating multiple sclerosis and/or other demyelinating diseases is disclosed. Disclosed are also pharmaceutical compositions for treating multiple sclerosis and/or other demyelinating diseases. Disclosed are also pharmaceutical compositions for the simultaneous, separate or sequential use of its active ingredients for the above specified therapy. In particular, the advantage of EP0003504 of GH together with IFN-β to produce a pharmaceutical composition for the treatment of multiple sclerosis are shown.

12 Claims, 2 Drawing Sheets

OTHER PUBLICATIONS

Yao et al., Insulin–like growth factor–I given subcutaneously reduces clinical deficits, decreases lesion severity and upregulates synthesis of myelin proteins in experimental autoimmune encephalomyelitis, *Life Sciences*, 58:(16)1301–1306 (1996).

Yao et al., Cryogenic spinal cord injury induces astrocytic gene expression of insulin–like growth factor I and insulin–like growth factor binding protein 2 during myelin regeneration, *Journal of Neuroscience Research*, 40:647–659 (1995).

Ussing, Zinc in the anterior pituitary of rat: a histochemical and analytical work, *Neuroendocrinology*, 45:233–242 (1987).

Singh et al., Modified forms of human growth hormone with increased biological activities, *Endo*, 94(3):883–891 (1981).

Shepard et al., A single amino acid change in IFN–$\beta_1$ abolishes its antiviral activity, *Nature*, 294:563–566 (1981).

Martia et al., Human growth hormone: complementary DNA cloning and expression in bacteria, *Science*, 205:602–607 (1979).

Mark et al., Site–specific mutagenesis of the human fibroblast interferon gene, *Proc. Natl. Acad. Sci. USA*, 81:5662–5666 (1984).

Quigeley et al., Chronic relapsing experimental autoimmune encephalomyelitis: effects of insulin–like growth factor–I treatment on clinical deficits, lesion severity, glial responses, and blood brain barrier defects, *Journal of Neuropathology and Experimental Neurology*, 57:426–438 (1998).

Lewis et al., Altered proteolytic cleavage of human growth hormone as a result of deamidation, *The Journal of Biological Chemistry*, 11645–11650 (1981).

Lewis et al., A naturally occurring structural variant of human, *The Journal of Biological Chemistry*, 253:2679–2687 (1978).

Lewis et al., Enhancement of the hyperglycemic activity of human growth hormone by enzymic modification, *Endo*, 101(5)1587–1603 (1977).

Komoly et al., Insulin–like growth factor I gene expression is induced in astrocytes during experimental demyelination, *Proc. Natl. Acad. Sci. USA*, 89: 1894–1898 (1992).

Hsiung et al., Use of bacteriocin release protein in *E. coli* for excretion of human growth hormone into the culture medium, Bio/Technology, 7:267–271 (1989).

Graf et al., Human somatotropin, *The Journal of Biological Chemistry*, 257:2365–2369 (1982).

Goeddel et al., Direct expression in *Escherichia coli* of a DNA sequence coding for human growth hormone, *Nature*, 281:544–548 (1979).

Gertler et al., Inhibition of lactogenic activities of ovine prolactin and human growth hormone (hGH) by a novel form of a modified recombinant hGH, *Endo*, 118:720–726 (1986).

Galli et al., Apoptosis in cerebellar granule cells is blocked by high KCL, forskolin, and IGF–1 through distinct mechanisms of action: The involvement of intracellular calcium and RNA synthesis, *The Journal of Neuroscience*, 15(2):1172–1179 (1995).

Fernandez et al., Insulin–like growth factor I restores motor coordination in a rat model of cerebellar ataxia, *Proc. Natl. Acad. Sci. USA*, 95:1253–1258 (1998).

Dore et al., Rediscovering an old friend, IGF–1: potential use in the treatment of neurodegenerative diseases, *TINS*, 20(8):326–331 (1997).

Derynck et al., Isolation and structure of a human fibroblast interferon gene, *Nature*, 285:542–547 (1980).

De Pablo et al., The developing CNS: a scenario for the action of proinsulin, insulin and insulin–like growth factors, *TINS*, 18:143–151 (1995).

DeNoto et al., Human growth hormone DNA sequence and mRNA structure: possible alterative splicing, *Nucleic Acids Research*, 9:3719–3731 (1981).

Chen et al., The human growth hormone locus: nucleotide sequence, biology, and evolution, *Genomics*, 4:479–497 (1989).

Bewley et al., Sequence comparison of human pituitary growth hormone, human chronic somatomammotropin, and ovine pituitary growth and lactogenic hormones, *Int. J. Peptide Protein Res.*, 4:281–287 (1972).

Becker et al., Isolation and characterization of a sulfoxide and a desamido derivative of biosynthetic human growth hormone, *Biotechnology and Applied Biochemistry*, 10:326–337 (1988).

ARTICLES—Randomised double–blind placebo–controlled study of interferon β–1a in relapsing/remitting multiple sclerosis, *Lancet*, 352:1498–1504 (1998).

* cited by examiner

US 6,869,600 B1

COMBINED TREATMENT OF MULTIPLE SCLEROSIS

REFERENCE TO RELATED APPLICATION

The present application is the national stage under 35 U.S.C. 371 of international application PCT/EP00/02443, filed Mar. 20, 2000 which designated the United States, and which international application was published under PCT Article 21(2) in the English language.

FIELD OF THE INVENTION

The present invention relates to the use of growth hormone (GH) together with an interferon (IFN) to produce a pharmaceutical composition for treating multiple sclerosis and/or other demyelinating diseases. It also relates to said pharmaceutical compositions for the simultaneous, separate or sequential use of its active ingredients for the above specified therapy.

In particular, it relates to the use of GH together with IFN-β to produce a pharmaceutical composition for the treatment of multiple sclerosis.

BACKGROUND OF THE INVENTION

Multiple sclerosis (MS) is a slowly progressive CNS disease characterized by disseminated patches of demyelination in the brain and spinal cord, resulting in multiple and varied neurologic symptoms and signs, usually with remissions and exacerbation (see The Merk Manual, sixteenth edition).

The cause is unknown but an immunologic abnormality is suspected, with few clues presently indicating a specific mechanism. Postulated causes include infection by a slow or latent virus, and myelinolysis by enzymes. IgG is usually elevated in the CSF, and elevated titers have been associated with a variety of viruses, including measles. The significance of these findings and of reported associations with HLA allotypes and altered number of T cells is unclear, and the evidence somewhat conflicting. An increased family incidence suggests genetic susceptibility, women are somewhat more often affected than men. Environmental factors seem to be present. Although age at onset generally is from 20 to 40 years, MS has been linked to the geographic area where a patient's first 15 years are spent. Relocation after age 15 does not alter the risk.

Plaques or islands of demyelination with destruction of oligodendroglia and perivascular inflammation are disseminated through the CNS, primarily in the white matter, with a predilection for the lateral ad posterior columns (especially in the cervical and dorsal regions), the optic nerves, and periventricular areas. Tracts in the midbrain, pons, and cerebellum also are affected, and gray matter in both cerebrum and cord may be affected.

Cell bodies and axons are usually preserved, especially in early lesions. Later, axons may be destroyed, especially in the long tracts, and a fibrous gliosis gives the tracts their "sclerotic" appearance. Both early and late lesions may be found simultaneously. Chemical changes in lipid and protein constituents of myelin have been demonstrated in and around the plaques.

The disease is characterized by various complaints and findings of CNS dysfunction, with remissions and persistently recurring exacerbations.

Magnetic Resonance Imaging (M) is the most sensitive diagnostic imaging technique; it may show many plaques. Lesions also may be visible on contrast enhanced to CT scans.

Therapeutic advances in multiple sclerosis (MS) have been slow to emerge, partly because of incomplete understanding of the pathogenesis of the disorder. For empirically based treatment the major obstacles to progress include the highly variable course of MS, the long-term nature of the most important outcome measures, and the lack of objective markers of treatment effect, particularly in the short term.

Although the pathogenesis of MS remains uncertain, the natural history continues to be studied. Objective outcome measures based on magnetic resonance imaging (MRI) have been developed and many of the pitfalls of clinical trials are now known, which has led to improved trial methods and better interpretation of results.

Interferons are a subclass of cytokines that exhibit both antiviral and antiproliferative activity. On the basis of biochemical and immunological properties, the naturally-occurring human interferons are grouped into three classes: interferon alpha (leukocyte), interferon beta (fibroblast) and interferon gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential antitumour and antiviral activities.

The three major IFNs are referred to as IFN-α IFN-β and TFN-γ. Such main kinds of IFNs were initially classified according to their cells of origin (leucocyte, fibroblast or T cell). However, it became clear that several types may be produced by one cell. Hence leucocyte IFN is now called IFN-α, fibroblast IFN is IFN-β and T cell IFN is IFN-γ. There is also a fourth type of IFN, lymphoblastoid IFN, produced in the "Namalwa" cell line (derived from Buikitt's lymphoma), which seems to produce a mixture of both leucocyte and fibroblast IFN.

The Interferon unit has been reported as a measure of IFN activity defined (somewhat arbitrarily) as the amount necessary to protect 50% of the cells against viral damage.

Every class of IFN contains several distinct types. IFN-β and IFN-γ are each the product of a single gene. The differences between individual types seem to be mainly due to variations in glycosylation.

IFNs-α are the most diverse group, containing about 15 types. There is a cluster cell of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. In effect, these new types of therapeutic agents can be called biologic response modifiers (BRMs), because they have an effect on the response of the organism to the tumour, affecting recognition via immunomodulation.

In particular, human fibroblast interferon (IFN-α) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, Derynk et al. (Derynk R. et al., *Nature* 285, 542–547, 1980) deduced the complete amino acid sequence of the protein. It is 166 amino acid long.

Shepard et al. (Shepard H. M. et al., *Nature,* 294, 563–565, 1981) described a mutation at base 842 (Cys→Tyr at position 141) that abolished its anti-viral activity, and a variant clone with a deletion of nucleotides 1119–1121.

Mark et al. (Mark D. F. et al., *Proc. Natl. Acad. Sci. U.S.A.,* 81 (18) 5662–5666, 1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

Rebif® (recombinant human Interferon-β) is the latest development in interferon therapy for multiple sclerosis (MS) and represents a significant advance in treatment. Rebif® is interferon (IFN)-beta 1a, produced from mammalian cell lines and virtually identical to the naturally occurring human molecule.

The mechanisms by which IFNs exert their effects are not completely understood. However, in most cases they act by affecting the induction or transcription of certain genes, thus affecting the immune system. In vitro studies have shown that IFNs are capable of inducing or suppressing about 20 gene products.

IFN-β may act by three major pathways in MS:
  a regulation of T-cell functions such as activation, proliferation and suppressor cell function;
  modulation of the production of cytokines: down-regulation of proinflammatory cytokines and up-regulation of inhibitory, antiinflammatory cytokines;
  regulation of T-cell migration and infiltration into the CNS via the BBB (blood brain barrier).

The PRISMS study has established the efficacy of Interferon beta-1a given subcutaneously three times per week in the treatment of Relapsing-Remitting Multiple Sclerosis (RR-MS). This study showed that Interferon beta-1a can have a positive effect on the long-term course of MS by reducing number and severity of relapses and reducing the burden of the disease and disease activity as measured by MRI. (Randomised, Double-Blind, Placebo-Controlled Study of Interferon beta-1a in Relapsing-remitting Multiple Sclerosis", The Lancet 1998; 352 (7 Nov., 1998): 1498–1504.)

Human growth hormone, also known as somatotropin, is a protein hormone produced and secreted by the somatotropic cells of the anterior pituitary. Secretion is regulated by a releasing factor, i.e., the growth hormone-releasing hormone (GHRH), and by an inhibitory factor, somatostatin. Human growth hormone plays a key role in somatic growth through its effects on the metabolism of proteins, carbohydrates and lipids.

Human growth hormone is a single polypeptide chain of 191 amino acids (Bewly et al, 1972) having two disulfide bonds, one between Cys-53 and Cys-165, forming a large loop in the molecule, and the other between Cys-182 and Cys-189, forming a small loop near the C-terminus. The DNA sequence that confirmed the amino acid sequence was to reported by Martial et al (1979). Purified hGH is a white amorphous powder in its lyophilized form. It is readily soluble (concentrations >10 mg/L) in dilute aqueous buffers at pH greater than 7.2.

In solution, hGH exists predominantly as a monomer, with a small fraction as dimers and higher molecular weight oligomers. Under certain conditions, hGH can be induced to form larger amounts of dimers, trimers and higher oligomers.

Several derivatives of hGH are known, including naturally-occurring derivatives, variants and metabolic products, degradation products primarily of biosynthetic hGH and engineered derivatives of hGH produced by genetic methods. One example of a naturally-occurring derivative of hGH is GH-V, a variant of growth hormone found in the placenta. Other members of the gene locus are described in Chen et al (1989). Any derivative of hGH, including derivatives designed to be long-lasting in the body, can be used for the purpose of the present invention as long as it retains the biological activity of hGH.

Methionyl hGH was the first form of hGH to be produced through recombinant DNA technology. This compound is actually a derivative of hGH having one additional methionine residue at its N-terminus (Goeddel et al, 1979).

A naturally-occurring variant of hGH called 20K-hGH has been reported to occur in the pituitary as well as in the bloodstrein (Lewis et al, 1978; Lewis et al., 1980). This compound, which lacks the 15 amino acid residues from Glu-32 to Gln-46, arises from an alternative splicing of the messenger ribonucleic acid (DeNoto et al, 1981). This compound shares many, but not all of the biological properties of hGH.

20K-HGH is made in the pituitary and secreted into the blood. It makes up about 5% of growth hormone output of adults, and about 20% of growth hormone output of children. It has the same growth promoting activity as 22 kD growth hormone, and has been reported to have equal to or greater the amount of lipolytic activity as the 22 kD form. It binds to growth hormone receptors with equal affinity as the 22 kD growth hormone, and has one tenth the lactogenic (prolactin-like) bioactivity as the 22 kD hormone. Unlike 22 kD, the 20-k-HGH has weak anti-insulin activity.

GH regulates the secretion of Insulin-like Growth Factor (IGF-1) which accounts for most of its biological activity. The following effects of IGF-I on myelination are also known:
1) in vitro: IGF-1 promotes
   a) proliferation of oligodendrocyte precursors
   b) survival and differentiation of mature oligodendrocytes
2) in vivo
   a) Transgenic mice overexpressing IGF-1 have more oligodendrocytes (2030%), more myelinated axons and thicker myelin than wt animals
   b) IGF-1 Knock-Out (KO) mice and IGF-BP1 overexpressors are hypomyelinated (This also true of GH KO)
3) During remyclination (following Experimental Autoimmune Encephalomyelitis (EAE) or Spinal cord injury):
   a) expression of the receptor 1 for IGF-1 is upregulated in oligodendrocytes
   b) expression of IGF-1 is upregulated in astrocytes
4) IGF-1 iv reduces
   a) demyelination in rat Experimental Auto immune Encephalomyclitis (induced by guinea Pig spinal cord homogenates)
   b) immune cell entry into the parenchyma in an adoptive transfer model of EAE. Recombinant human growth hormone, rhGH, is produced by Serono Laboratories, Inc., as SEROSTIM®, which product has been given accelerated FDA approval for treating weight loss and wasting in AIDS patients. PROTROPIN®, produced by Genentech, Inc. (South San Francisco, Calif.), differs slightly in structure from natural sequence hGH, having an additional methionine residue at the N-terminus.

DESCRIPTION OF THE INVENTION

The present patent application is based on the assumption that the coadministration of GH in the treatment of MS or other demyelinating diseases, favouring remyelination, reinforces the effect of an interferon, which is thought to act mainly as an inhibitor of inflammation, thus achieving a synergistic effect. This assumption is based on the last findings by the Applicant that the administration of GH in combination with IFN-α has beneficial effect on remyelination and significantly reduces clinical signs of the disease in an experimental animal model; a synergistic effect of the two active ingredients is also shown.

Therefore, the main object of the present invention is the use of GH in combination with an interferon to produce a pharmaceutical composition for treating MS and/or other demyelinating diseases. The GH and the interferon can be administered simultaneously, separately or sequentially.

Another object of the present invention is, therefore, the method for treating by administering simultaneously, separately or sequentially an effective amount of GH and an effective amount of an interferon, together with a pharmaceutically acceptable excipient.

An "effective amount" refers to an amount of the active ingredients that is sufficient to affect the course and the severity of the disease, leading to the reduction or remission of such pathology. The effective amount will depend on the route of administration and the condition of the patient.

A further object of the present invention are the pharmaceutical compositions containing GH and an interferon, in the presence of one or more pharmaceutically acceptable excipients, for the simultaneous, separate or sequential administration of its active ingredients for treating MS and/or other demyelinating diseases.

In general, pharmaceutical compositions as contemplated according to the present invention comprise effective amounts of protein or derivative products of the invention together with pharmaceutically acceptable diluents, stabilizers, preservatives, solubilizers, emulsifiers, adjuvants and/or carriers; see, e.g., Remington's Pharmaceutical Sciences, 18th Ed. (1990, Mack Publishing Co., Easton, Pa. 18042) pages 1435–712. An effective amount of active ingredient is a therapeutically, prophylactically, or diagnostically effective amount, which can be readily determined by a person skilled in the art by taking into consideration such factors as body weight, age, therapeutic or prophylactic or diagnostic goal, and release rate desired.

In case of separate or sequential use of the two active ingredients, the pharmaceutical compositions of the invention will consist of two different formulations, each comprising one of the two active ingredients together with one or more pharmaceutically acceptable excipients.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

The administration of such active ingredients may be by intravenous, intramuscular or subcutaneous route. Other routes of administration, which may establish the desired blood levels of the respective ingredients, are comprised by the present invention.

The combined therapy of the present invention is suitable for treating MS and/or other demyelinating diseases.

The tern "human growth hormone", as used in the present invention, is intended to include the naturally-occurring derivatives, as noted above, including, without limitation, both the 20 kD and the 22 kD human growth hormone, GH-V, and other members of the growth hormone gene locus as described in Chen et al (1989). The term also includes functional derivatives, fragments, variants, analogs, or salts which retain the biological activity of growth hormone, i.e., which act as agonists to the growth hormone receptor. In other words, they are capable of binding to the growth hormone receptor to initiate the signaling activity of the receptor.

A number of derivatives of hGH arise from proteolytic modifications of the molecule. The primary pathway for the metabolism of hGH involves proteolysis. The region of hGH around residues 130–150 is extremely susceptible to proteolysis, and several derivatives of hGH having nicks or deletions in this region have been described (Thorlacius-Ussing, 1987). This region is in the large loop of hGH, and cleavage of a peptide bond there results in the generation of two chains that are connected through the disulfide bond at Cys-53 and Cys-165. Many of these two-chain forms are reported to have increased biological activity (Singh et al, 1974). Many derivatives of human growth hormone have been generated artificially through the use of enzymes. The enzymes trypsin and subtilisin, as well as others, have been used to modify hGH at various points throughout the molecule (Lewis et al, 1977; Graff et al, 1982). One such derivative, called two-chain anabolic protein (2-CAP), was formed through the controlled proteolysis of hGH using trypsin (Becker et al, 1989). 2-CAP was found to have biological properties very distinct from those of the intact hGH molecule, in that the growth-promoting activity of hGH was largely retained and most of the effects on carbohydrate metabolism were abolished.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, 1981). Deamidated hGH has been shown to have an altered susceptibility to proteolysis with the enzyme subtilisin, suggesting that deamidation may have physiological significance in directing proteolytic cleavage of hGH. Biosynthetic hGH is known to degrade under certain storage conditions, resulting in deamidation at a different asparagine (Asn-149). This is the primary site of deamidation, but deamidation at Asn-152 is also seen (Becker et al, 1988). Deamidation at Gln-137 has not been reported in biosynthetic hGH.

Methionine residues in proteins are susceptible to oxidation, primarily to the sulfoxide. Both pituitary-derived and biosynthetic hGH undergo sulfoxidations at Met-14 and Met-125 (Becker et al, 1988). Oxidation at Met-170 has also been reported in pituitary but not biosynthetic hGH. Both desamide hGH and Met-14 sulfoxide hGH have been found to exhibit full biological activity (Becker et al, 1988).

Truncated forms of hGH have been produced, either through the actions of enzymes or by genetic methods.

2-CAP, generated by the controlled actions of trypsin, has the first eight residues at the N-terminus of hGH removed. Other truncated versions of hGH have been produced by modifying the gene prior to expression in a suitable host. The first 13 residues have been removed to yield a derivative having distinctive biological properties (Gertler et al, 1986) in which the polypeptide chain is not cleaved.

Although human growth hormone was originally obtained firm pituitary glands of cadavers, these preparations were not electrophoretically homogeneous, and antibodies appeared in the serum of patients treated with preparations of the order of 50% purity, the immunogenicity being attributed to inactive components. Recombinant DNA technology permitted production of an unlimited supply of hGH in a number of different systems.

Purification of hGH from the culture medium is facilitated by the presence of only low amounts of contaminating proteins. In fact, it has been shown that hGH can be purified on a laboratory scale by a single purification step on a reversed-phase HPLC column (Hsiung et al (1989).

Recombinant hGH is generally marketed as vials containing hGH plus additional excipients, e.g., glycine and mannitol, in a lyophilized form. A companion diluent vial is provided, allowing the patient to reconstitute the product to the desired concentration prior to administration of the dose. Recombinant hGH can also be marketed in other well known manners, such as prefilled syringes, etc.

The term "interferon", as used in the present patent application, is intended to include any molecule defined as such in the literature, comprising for example any kinds of IFNs mentioned in the above section "background of the Invention". In particular, any kinds of IFN-α, IFN-β and IFN-γ are included in the above definition. IFN-β is the preferred IFN according to the present invention.

The term "interferon-beta (IFN-β)", as used in the present invention, is intended to include human fibroblast interferon, as obtained by isolation from biological fluids or as obtained by DNA recombinant techniques from prokaryotic or eukaryotic host cells as well as its salts, functional derivatives, variants, analogs and fragments.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the proteins as described above, i.e., the ability to bind the corresponding receptor and initiate receptor signaling, and do not confer toxic properties on compositions containing it. Derivatives may have chemical moieties, such as carbohydrate or phosphate residues, provided such a derivative retains the biological activity of the protein and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the molecule in body fluids.

Of particular importance is a protein that has been derivatized or combined with a complexing agent to be long lasting. For example, pegylated versions, or proteins genetically engineered to exhibit long lasting activity in the body, can be used according to the present invention.

The term "derivatives" is intended to include only those derivatives that do not change one amino acid to another of the twenty commonly-occurring natural amino acids.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (hGH and IFN-beta, respectively) relevant to the present invention, i.e., the ability to bind to the corresponding receptor and initiate receptor signaling.

A "fragment" according to the present invention refers to any subset of the molecules, that is, a shorter peptide which retains the desired biological activity. Fragments may readily be prepared by removing amino acids from either end of the molecule and testing the resultant for its properties as a receptor agonist. Proteases for removing one amino acid at a time from either the N-terminal or the C-terminal of a polypeptide are known, and so determining fragments which retain the desired biological activity involves only routine experimentation.

Additionally, the polypeptide which has such hGH receptor agonist activity, be it hGH, an analog or variant, salt, functional derivative or fragment thereof, can also contain additional amino acid residues flanking the hGH polypeptide. As long as the resultant molecule retains the hGH receptor agonist ability of the core polypeptide, one can determine whether any such flanking residues affect the basic and novel characteristics of the core peptide, i.e., its receptor agonist characteristics, by routine experimentation. The tern "consisting essentially of", when referring to a specified sequence, means that additional flanking residues can be present which do not affect the basic and novel characteristic of the specified sequence. This term does not comprehend substitutions, deletions or additions within the specified sequence.

A "variant" according to the present invention refers to a molecule which is substantially similar to either the entire proteins defined above or a fragment thereof. Variant peptides may be conveniently prepared by direct chemical synthesis of the variant peptide, using methods well known in the art. Of course, such variant would have similar receptor binding and signal initiating activity as the corresponding naturally-occurring protein.

Amino acid sequence variants of the proteins defined above (both GH and/or an interferon) can be prepared by mutations in the DNAs which encode the synthesized derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure.

At the genetic level, these variants ordinarily are prepared by site-directed mutageneis of nucleotides in the DNA encoding the peptide molecule, thereby producing DNA encoding the variant, and thereafter expressing the DNA in recombinant cell culture. The variants typically exhibit the same qualitative biological activity as the non-variant peptide.

A special kind of interferon variant has been described recently. The so-called "consensus interferons" are non-naturally occurring variants of IFN (U.S. Pat. No. 6,013,253). Consensus interferons were shown to be effective in the treatment of multiple sclerosis.

Therefore, in a preferred embodiment of the invention, growth hormone is used in combination with a consensus interferon to produce a pharmaceutical composition for treating multiple sclerosis and/or other demyelinating diseases.

As used herein, human interferon consensus (IFN-con) means a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not extant in that position in at least one naturally-occurring subtype. IFN-con encompasses but is not limited to the amino acid sequences designated IFN-con.sub.1, IFN-con.sub.2 and IFN-con.sub.3 which are disclosed in U.S. Pat. Nos. 4,695,623, 4,897,471 and 5,541,293. DNA sequences encoding IFN-con may be produced as described in the above-mentioned patents or other standard methods. Preferably, they are produced recombinantly.

An "analog" of the proteins defined above (both GH and/or an interferon), according to the present invention, refers to a non-natural molecule which is substantially similar to either the entire molecules or to an active fragment thereof. Such analog would exhibit the same activity as the corresponding naturally-occurring protein.

The types of substitutions which may be made in the human growth hormone and/or in an interferon, according to the present invention, may be based on analysis of the frequencies of amino acid changes between a homologous protein of different species. Based upon such analysis, conservative substitutions may be defined herein as exchanges within one of the following five groups:

Small, aliphatic, non-polar or slightly polar residues:
   Ala, Ser, Thr, Pro, Gly
II. Polar, negatively-charged residues and their amides:
   Asp, Asn, Glu, Gin
III. Polar, positively-charged residues:
   His, Arg, Lys
IV. Large, aliphatic nonpolar residues:
   Met, Leu, lie, Val, Cys
V. Large aromatic residues:
   Phe, Try, Trp.

Within the foregoing groups, the following substitutions are considered to be "highly conservative":
   Asp/Glu
   His/Arg/Lys
   Phe/Tyr/Trp
   Met/Leu/Ile/Val.

Semiconservative substitutions are defined to be exchanges between two of groups (I)–(IV) above which are limited to supergroup (A), comprising (I), (II), and (III) above, or to supergroup (B), comprising (IV) and (V) above. Substitutions are not limited to the genetically encoded or even the naturally-occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-5-imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide is also useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and ε-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)]carbodiimide or 1-ethyl-34-azonia-4,4-dimethylpentylcarbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Examples of production of amino acid substitutions in proteins which can be used for obtaining analogs for use in the present invention include any known method steps, such as presented in U.S. patent RE 33,653; U.S. Pat. Nos. 4,959,314; 4,588,585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

Preferably, the variant or analog, as defined above, will have a core sequence, which is the same as that of the "native" sequence or biologically active fragment thereof, which has an amino acid sequence having at least 70% identity to the native amino acid sequence and retains the biological activity thereof. More preferably, such a sequence has at least 80% identity, at least 90% identity, or most preferably at least 95% identity to the native sequence.

The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs or variants in accordance with the present invention may also be determined in accordance with the following procedure. The DNA of the native sequence is known to the prior art and is found in the literature (Martial et al, 1979). Polypeptides encoded by any nucleic acid, such as DNA or RNA, which hybridizes to the complement of the native DNA or RNA under highly stringent or moderately stringent conditions, as long as that polypeptide maintains the biological activity of the native sequence, are also considered to be within the scope of the present invention.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al., (1984) for determining the stability of hybrids of 100% identity expressed as melting temperature Tm of the DNA—DNA hybrid: Tm=81.5° C.+16.6 ($_{Log}$M)+0.41 (% GC)−0.61 (% form)−500/L, where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 1000% hybrid according to equation of Meinkoth, hybridization will occur even if there is up to about 10% mismatch.

As used herein, highly stringent conditions are those which are tolerant of up to about 15% sequence divergence, while moderately stringent conditions D those which are tolerant of up to about 20% sequence divergence. Without limitation, examples of highly stringent (12–15° C. below the calculated Tm of the hybrid) and moderately (15–20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions, is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 μg/ml denatured, fragmented salmon sperm DNA at a temperature approximately 20° to 25° C. below the Tm. If mixed probes are used, it is preferable to use tetramethyl ammonium chloride (iMAC) instead of SSC (Ausubel, 1987–1998).

While the present invention provides recombinant methods for making the above-defined derivatives, these derivatives may also be made by conventional protein synthesis methods which are well known to those skilled in the art.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention. The Examples will refer to the Figures specified here below.

Effect of GH treatment on time course of mean clinical of MOG-induced EAE in mice. Mice were immunized with 200 μg of MOG35-55 peptide in CFA, and given 500 ng pertussis toxin ip immediately and two days later. Animals received a boost consisting of an identical amount of peptide in CFA a week later. Mean clinical scores (±SEM) of groups injected daily with either saline or recombinant human growth hormone 2 mg/kg s.c. from onset of disease to day 31 of treatment are shown. Statistical analyses of area under the curve has shown the one-tailed P value of 0.02, considered significant using either the unpaired t-test as well as the Mann-Whitney test.

FIG. 2

Figure 1:
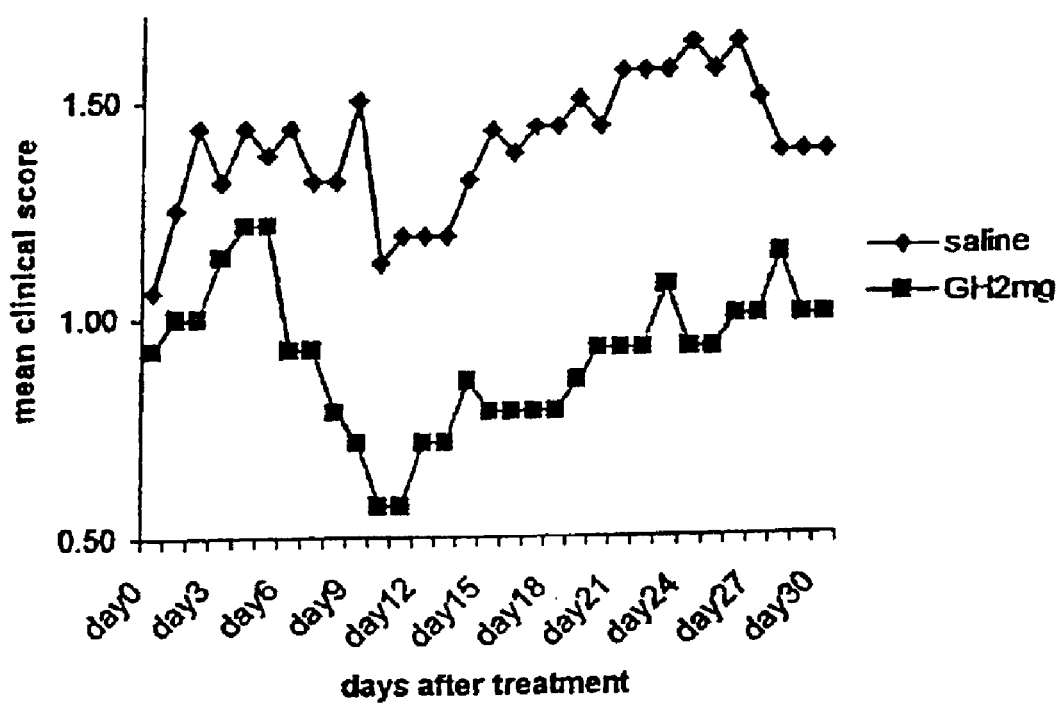
FIG. 1

Synergistic effect of GH treatment and IFN-beta on the time course of MOG-induced EAE in mice. Animals were immunized as described in the description of FIG. 1. Mean clinical scores (±SEM) of mice injected with recombinant human growth hormone at 1 mg/kg from onset to day 33 of disease are not statistically different from saline injected controls, while recombinant murine IFNbeta significantly decrease mean clinical scores as analysed by area under the curve (the one-tailed P value is 0.0076). However, when combined with IFNb, rhGH at a dose that had no effect by itself, could significantly decrease neurological disease in mice as reflected by mean clinical scores using analyses of area under the curve by unpaired T-test (the one-tailed P value is 0.02, considered significant for IFN×GH+IFN.

EXAMPLES

We have tested the hypothetical beneficial effect of GH on remyelination using the experimental autoimmune encephalomyclitis model, which is a chronic demyelinating model.

EAE Induction Protocol

Experimental autoimmune encephalomyelitis (EAE) has been induced in groups of mice as follows below. Groups of C57black6/J female mice are immunized subcutaneously into the right flank at day 0 with 200 μl emulsion, containing 200 μg of a synthetic peptide corresponding to Myelin Oligodendrocyte Glycoprotein (MOG 35-55) (Neosystem) in Complete Freunds Adjuvant containing 5 mg/ml H37RA *Mycobaterium tuberculosis.*

Immediately, and at day 2, mice receive an intraperitoneal injection of 500 ng pertussis toxin dissolved in 400 μl pertussis buffer (0.5M NaCl, 0.015M Tris pH 7.5, 0.017%

Triton X-100). At day 7 mice receive a boost of identical amount (200 µl) or emulsion, containing 200 µg MOG35-55 peptide in Complete Freund's Adjuvant, into the left flank this time.

The animals showing a definite sign of neurological impairment reflected by a tail paralysis have started to be treated daily with 200 µl of either:
1) phosphate buffered saline (PBS) (n=9/8),
2) human recombinant growth hormone at 1 or 2 mg/kg (only, when administered alone) (n=9),
3) recombinant murine interferon beta at 10,000 IU (n=0/9), or the
4) combined rhGH and rmIFbeta.

PBS has been used as vehicle and all substances have been injected subcutaneously in the neck, whereby the group treated with two substances was injected twice into two different sites.

Animals have been scored daily for neurological signs according to the previously described scale.

The time course of mean clinical scores SEM of each group are represented bellow, and P<0.05 for all treatments except for GH×PBS, using Mann-Whitney test analysis.

Control group received only the vehicle (CFA). Weight loss and clinical score of individual animals has been monitored daily up to day 43 after immunization, using international standard of scoring by following criteria:
0=no signs of disease
1=tail weakness or paralysis
2=tail paralysis+hindlimb(s) weakness or partial paralysis
3=tail paralysis+complete hindlimb paralysis
3.5=tail paralysis+hindlimb paralysis+incontinence
4=tail paralysis+hindlimbs paralysis+weakness or paralysis of forelimbs
5=moribund
P<0.05: The one-tailed P value is considered significant. T-test.

Results

We have tested the effects of recombinant human growth hormone (rhGH) in the previously described EAE model. RhGH when administered daily to diseased animals has been effective in decreasing the neurological signs of disease over 30 days of treatment at doses of 2 mg/kg subcutaneously. The results are reported in FIG. 1.

Figure 2:
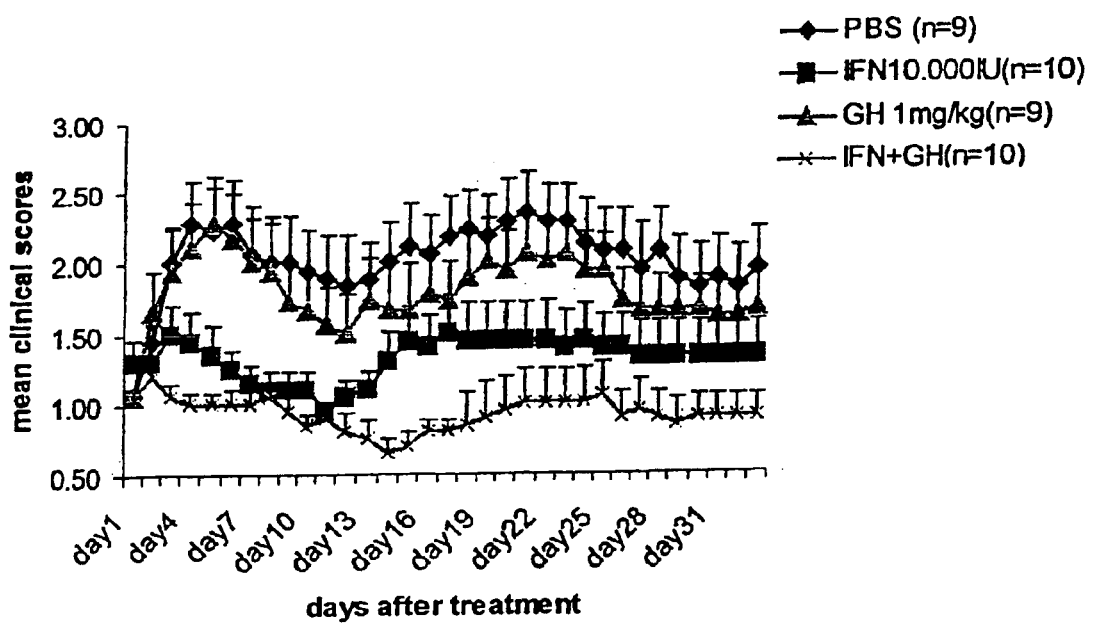

The results achieved with the combined therapy (rhGH plus rmIFN-β) are shown in FIG. 2.

CONCLUSIONS

Our results show a clear beneficial effect of GH treatment, which reduces clinical signs of chronic EAE in mice after immunization with MOG. Therefore, GH has a beneficial therapeutic effect, and can be used as treatment, in chronic demyelinating diseases such as MS; in particular, a synergistic effect with IFN-β is shown.

REFERENCES

Anonymus, *The Lancet* 352, 1498–1504, (1998);
Becker et al, *Biotechnol. Appl. Biochem.* 10, 326 (1988);
Becker et al., *Abstract. No.* 342, 71 st Annual Meeting, The Endocrine Society, Seattle, Wash., June 1989;
Bewly et al., *Int. J. Peptide and Protein Res.* 4, 281–287 (1972);
Chen et al, *Genomics* 4, 479–497 (1989);
DeNoto et al, *Nucleic Acids Res.* 9, 3719 (1981)
dePablo F., TINS 18, 143 (1995) Derynk R. et al., *Nature* 285, 542–547, 1980;
Dore S., *TINS* 20, 326 (1997);
Fernandez A. M., *PNAS* 95, 1253 (1998);
Galli C. J., *Neurosc.* 15: 1172 (1995);
Gertler et al, *Endocrinology* 118, 720 (1986);
Goeddel et al., *Nature,* 281, 544 (1979);
Graff et al, *J. Biol. Chem.,* 257, 2365 (1982);
Hsiung et al, *Biotechnology,* 7, 267 (1989);
Komoly S., *PNAS,* 89, 1894;
Lewis et al, *Endocrinology* 101, 1587 (1977);
Lewis et al., *J. Biol. Chem.* 253, 2679 (1978)
Lewis et al, *J. Biol. Chem.* 256, 11645 (1981)
Li W, *J. Neuropath Exp Neurol.* 57, 426 (1998);
Mark D. F. et al., *Proc. Natl. Acad. Sci. U.S.A.,* 81 (18) 5662–5666 (1984); .
Marial et al, *Science,* 205, 602–607 (1979);
Remington's Pharmaceutical Sciences, 18th Ed. (1990, Mack Publishing Co., Easton Pa 18042), 1435–712;
Shepard H. M. et al., *Nature,* 294, 563–565, (1981);
Singh et al., *Endocrinology* 94, 883 (1974);
Thorlacius-Ussing, *Neuroendocrinology* 43, 233 (1987);
Yao D. L., *Life Sciences,* 58, 1301–1306 (1996);
Yao D. L., *J. Neurosc. Res.* 40, 647 (1995);
Yao D. L., *PNAS* 92, 6190 (1995);
Ye P., *J. Neurosc.* 15, 7344 (1995).

What is claimed is:

1. A pharmaceutical composition for use in producing remyelination comprising 1 mg/kq of a recombinant human growth hormone and 10,000 IU of interferon-β as active principles in combination with a pharmaceutically acceptable carrier, wherein the relative amounts of recombinant growth hormone and interferon-β are selected to provide synergistic remyelination results when administered to a patient in need thereof.

2. The pharmaceutical composition according to claim 1 which is in unit dosage form.

3. The pharmaceutical composition according to claim 1 which is in dosage form for subcutaneous administration.

4. A method for promoting remyelination in a patient in need thereof comprising administering to said patient 1 mg/kg of a recombinant human growth hormone and 10,000 IU of interferon-5 as active principles in the presence of one or more pharmaceutically acceptable excipient, wherein the relative amounts of the recombinant human growth hormone and interferon-β are selected to provide synergistic remyelination results.

5. The method according to claim 4 wherein the recombinant human growth hormone and the interferon-β are administered subcutaneously.

6. The method according to claim 4 wherein the recombinant human growth hormone and the interferon-β are administered sequentially.

7. The method according to claim 4 wherein the recombinant human growth hormone and the interferon-β administered separately.

8. The method according to claim 4 wherein the interferon-β is human recombinant interferon-β.

9. The method of claim 4 wherein said patient is suffering from multiple sclerosis.

10. The method of claim 9 wherein the GH and the interferon-A are administered simultaneously.

11. The method of claim 9 wherein the interferon-β is human recombinant interferon-β.

12. The method according to claim 9 wherein the recombinant growth hormone and the interferon-β are administered sequentially.

* * * * *